United States Patent [19]
Sugano et al.

[11] Patent Number: 5,834,257
[45] Date of Patent: Nov. 10, 1998

[54] α-AGARASE AND PRODUCTION PROCESS OF OLIGOSACCHARIDES AND MONOSACCHARIDES

[75] Inventors: Yasushi Sugano, Tokyo; Ichiro Terada, Kanagawa; Hisashi Kodama, Tokyo, all of Japan

[73] Assignee: Japan Tobacco Inc., Tokyo, Japan

[21] Appl. No.: 554,591

[22] Filed: Nov. 6, 1995

[51] Int. Cl.$^6$ .............................. C12P 19/04; C12P 19/12; C12N 9/24
[52] U.S. Cl. ............................ 435/101; 435/99; 435/100; 435/195; 435/200; 435/208
[58] Field of Search .................................. 435/200, 208, 435/195, 99, 100, 101

[56] References Cited

U.S. PATENT DOCUMENTS 5,418,156  5/1995  Stosz et al. ............................. 435/200

FOREIGN PATENT DOCUMENTS

| | | |
|---|---|---|
| 62-210955 | 9/1987 | Japan . |
| 62-210974 | 9/1987 | Japan . |
| 1-206923 | 8/1989 | Japan . |
| 2-65788 | 3/1990 | Japan . |
| 2-65789 | 3/1990 | Japan . |
| 3-37897 | 6/1991 | Japan . |
| 6-284888 | 10/1994 | Japan . |
| 7-163385 | 6/1995 | Japan . |
| 7-106148 | 11/1995 | Japan . |

OTHER PUBLICATIONS

Chemical Abstracts 85(7):42721w, 1976.
Aoki et al, Eur. J. Biochem., 187, pp. 461–465 (1990).
Belas, Journal of Bacteriology, vol. 171, No. 1, pp. 602–605 (Jan. 1989).
Belas et al, Applied and Environmental Microbiology, vol. 54, No. 1, pp. 30–37 (Jan. 1988).
Bibb et al, Journal of General Microbiology, 133, pp. 2089–2096 (1987).
Buttner et al, Mol Gen Genet, 209:101–109 (1987).
Day et al, Can. J. Microbiol., vol. 21, pp. 1512–1518 (1975).
Duckworth et al, Biochem. J., 113, pp. 687–692 (1969).
Duckworth et al, Biiochem. J., 113, pp. 693–696 (1969).
Fukasawa et al, Agric. Biol. Chem., 51 (1), pp. 265–268 (1987).
Fukasawa et al. Agric. Biol. Chem., 51 (1), pp. 269–270 (1987).
Groleàu et al, Can. J. Microbiol., vol. 23, pp. 672–679 (1977).
Hamer et al, Carbohydrate Research, 54, pp. C7–C10 (1977).
Hodgson et al, Journal of General Microbiology, 124, pp. 339–348 (1981).
Kendall et al, Gene, 29, pp. 315–321 (1984).
Leon et al., Applied and Environmental Microbiology, vol. 58, No. 12, pp. 4060–4063 (Dec. 1992).
Malmqvist, Biochimica et Biophysica Acta, 537, pp. 31–43 (1978).
Morrice et al, Eur. J. Biochem., 137, pp. 149–154 (1983).
Morrice et al. Eur. J. Biochem., 135, pp. 553–558 (1983).
Potin et al, Eur. J. Biochem., 214, pp. 599–607 (1993).
Rochas et al, Carbohydrate Research, 253, pp. 69–77 (1994).
Sugano et al, Journal of Bacteriology, vol. 176, No. 22, pp. 6812–6818 (Nov. 1994).
Sugano et al, Applied and Environmental Microbiology, vol. 59, No. 11, pp. 3750–3756 (Nov. 1993).
Sugano et al, Biochimica et Biophysica Acta, 1218, pp. 105–108 (1994).
Sugano et al, Journal of Fermentation and Bioengineering, vol. 79, No. 6, pp. 549–554 (1995).
Sugano et al, Applied and Environmental Microbiology, vol. 59, No. 5, pp. 1549–1554 (May 1993).
Van Der Meulen et al, Antonie van Leeuwenhoek, 42, pp. 81–94 (1976).
Yamaura et al, Agric. Biol. Chem., 55 (10), pp. 2531–2536 (1991).
Young et al, Carbohydrate Research, 66, pp. 207–212 (1978).
Tokunaga et al, Bioscience and Industry, vol. 49, No. 7, pp. 734–738 (1991).

*Primary Examiner*—Francisco C. Prats
*Attorney, Agent, or Firm*—Birch, Stewart, Kolsch & Birch, LLP

[57] ABSTRACT

The present inventions relate to novel α-agarase which selectively hydrolyzes the 1,3-bond of an oligosaccharide derived from agarose; a process for producing oligosaccharides and/or monosaccharides, characterized by that a β-agarase which acts on both polysaccharides and oligosaccharides derived from agarose and an α-agarase which acts specifically on oligosaccharides derived from agarose are allowed to react with a substrate which contains agarose or an oligosaccharide derived from agarose; and a process for producing oligosaccharides and/or monosaccharides, characterized by that the above α-agarase is allowed to react with a substrate which contains an oligosaccharide derived from agarose.

22 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( i v ) ANTI-SENSE: NO     ( x i ) SEQUENCE DESCRIPTION: SEQ ID NO:1:

Ala  Thr  Leu  Val  Thr  Ser  Phe
    1                       5

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide -continued (iii) HYPOTHETICAL: NO (iv) ANTI-SENSE: NO (xi) SEQUENCE DESCRIPTION: SEQ ID NO:2:

Ser Gly Thr Gly Ser Lys Leu Ser Leu Ala
1               5                   10

α-AGARASE AND PRODUCTION PROCESS OF OLIGOSACCHARIDES AND MONOSACCHARIDES

BACKGROUND OF THE INVENTION

1. Field of the Invention

The present inventions relate to novel α-agarase as well as a process for producing oligosaccharides and monosaccharides, derived from agar or agarose, which have effects of preventing aging of starch or products containing starch.

2. Description of the Prior Art

Starch and products containing starch are used as an adhesive agent, as well as food. However, when water is contained in those products, the flexibility of the products goes down due to an interaction between starch and water, resulting in aging phenomena. This directly causes deterioration such as hardening due to decreased capability to retain water in food, and cracking and the like due to drying in inedible products such as an adhesive. In order to inhibit these aging phenomena, many approaches have been done conventionally. For example, dextrin, sorbitol, fatty acid monoglyceride, lecithin and the like were added to food containing starch, and glycerine, formamide and the like to the inedible products have been done.

However, prevention of aging using the above additive agents is not perfect, and the use of formamide and the like accompanies dangers in term of the operating environment. For these reasons, development of more effective and highly safe age-resistant products have been desired.

In contrast, a report has been recently made that oligosaccharides derived from agar have a strong age resisting effect (JP-A 62-210955). The production process is characterized by that oligosaccharides and others are produced using conventional agarase such as agarase produced by *Pseudomonas sp.* N-7 (FERM P-9884 deposited to Fermentation Research Institute, Agency of Industrial Science and Technology which is presently called as National Institute of Bioscience and Human-Technology Agency of Industrial Science and Technology), or agarase produced by *Pseudomonas atlantica* manufactured by Sigma, with agar as the material, and that not less than 60% of the oligosaccharide liquid produced by this method comprises oligosaccharides of not less than 6 monosaccharide units and substances hardly degradable (JP-A 2-65788, JP-A 2-65789).

These degradation products of agarose derived from agar show a significant difference in age-resistant effects depending on the degree of polymerization. Specifically, oligosaccharides of not less than 20 monosaccharide units are not effective; it is necessary to use oligosaccharides of less than 6 monosaccharide units or monosaccharides in order to obtain sufficient effects (JP-A 62-210955, JP-A 62-210974, JP-B 3-37897). From this reason, it is necessary to selectively obtain oligosaccharides of a smaller degree of polymerization, so as to achieve more potential effects for preventing aging.

However, as described above, oligosaccharides of less than 6 monosaccharide units or not more than 5 monosaccharide units are obtained as little as not more than 40% of the product by conventional processes; it is hardly said that the effects of preventing aging are sufficiently achieved. In particular, regarding oligosaccharides having odd-number constituent monosaccharide units, such as those of 5 or 3 monosaccharide units and monosaccharides where greater effects may be expected, there is a problem in that these cannot be fundamentally produced by the action of conventional agarase.

OBJECTS AND SUMMARY OF THE INVENTION

The present inventors have studied intensively in view of the above-mentioned situation, and found that the above-mentioned problems can be solved by the following processes. Further, the present inventors found that a microorganism belonging to the genus of Vibrio produces novel α-agarase which selectively hydrolyzes the α-1,3 bond of an oligosaccharide derived from agarose and the α-agarase can be used in the present processes.

First Process

A process for producing oligosaccharides and/or monosaccharides, characterized by that a β-agarase which acts on both polysaccharides and oligosaccharides derived from agarose and an α-agarase which acts specifically on oligosaccharides derived from agarose are allowed to react with a substrate which contains agarose.

Second Process

A process for producing oligosaccharides and/or monosaccharides, characterized by that a β-agarase which acts on both polysaccharides and oligosaccharides derived from agarose and an α-agarase which acts specifically on oligosaccharides derived from agarose are allowed to react with a substrate which contains an oligosaccharide derived from agarose.

Third Process

A process for producing oligosaccharides and/or monosaccharides, characterized by that α-agarase which acts specifically on oligosaccharides derived from agarose is allowed to react with a substrate which contains an oligosaccharide derived from agarose.

Now, the present inventions are explained in details.

The First Process of the present invention is a process for producing oligosaccharides and/or monosaccharides, by allowing β-agarase which acts on both polysaccharide and oligosaccharides derived from agarose and α-agarase which acts specifically on oligosaccharides derived from agarose to react with a substrate containing agarose.

"Agarose" used in this method is a main polysaccharide component of agar, and is formed with D-galactose and 3,6-anhydro-L-galactose by way of repeating the α-1,3 bond and β-1,4 bond alternately.

A "substrate containing agarose" may consist of agarose alone or may be agarose to which oligosaccharides are added. The agarose concentration in solvent is preferably within a range of from 0.1% by weight to 1.0% by weight.

"β-agarase which acts on both polysaccharides and oligosaccharides derived from agarose (hereinafter referred to as "β-agarase A")" used in this method is β-agarase which hydrolyzes the β-1,4 bonds between D-galactose and 3,6-anhydro-L-galactose, and not particularly limited provided that the β-agarase acts on both polysaccharides and oligosaccharides derived from agarose.

"Oligosaccharide" in the present invention means a saccharide having constituent monosaccharide units not less than 2 and not more than 8; "polysaccharide" means a saccharide excluding monosaccharides and oligosaccharides. However, as the oligosaccharide as a substrate in the present invention, those having constituent monosaccharide units not less than 2 and not more than 6 are preferred.

As for the above-mentioned β-agarase A, those produced by a microorganism which belongs to the genus of Vibrio are preferred, and specifically, agarase 0107 derived from *Vibrio sp.* JT0107-L4 is enumerated.

The physical and chemical characteristics of agarase 0107, which is an example of such β-agarase A, are shown below.

(1) The enzymatic activity determination method

The amount of reducing sugars formed by an enzymatic reaction is measured by Somogyi-Nelson method. The details are as follows. Gel of 0.2% low-melting-point agarose (produced by Sigma) dissolved in 20 mM Tris-hydrochloric acid buffer (pH 8.0) is prepared. The substrate which uses 90 μl of this solution is mixed with 10 μl of a solution which contains β-agarase A. The mixture is incubated at 30° C. for 5 to 15 minutes, preferably for 5 minutes. After the incubation, 100 μl of copper reagent is added therein, and subjected to heating in boiling water for 10 minutes. After the heating, the solution is cooled rapidly in water. Therein, 100 μl of Nelson reagent is added, and then distilled water is added to make the total volume 2.5 ml. After 60 minutes, the absorbance at 660 nm is determined, and the determined value is converted to the amount of galactose. One U of the enzyme is defined as the amount that liberated 1 μmol of galactose per min under the conditions described above.

(2) Substrate specificity and function

At least a reaction which degrades agar and agarose in the endo style and makes the molecular weight low is catalyzed.

As for polysaccharides derived from agarose and oligosaccharides derived from agarose used as a substrate, the β-1,4 bond therein between D-galactose and 3,6-anhydro-L-galactose is hydrolyzed. In contrast, polysaccharides such as alginic acid and carageenan were not hydrolyzed.

(3) Optimum pH

Figure 1:
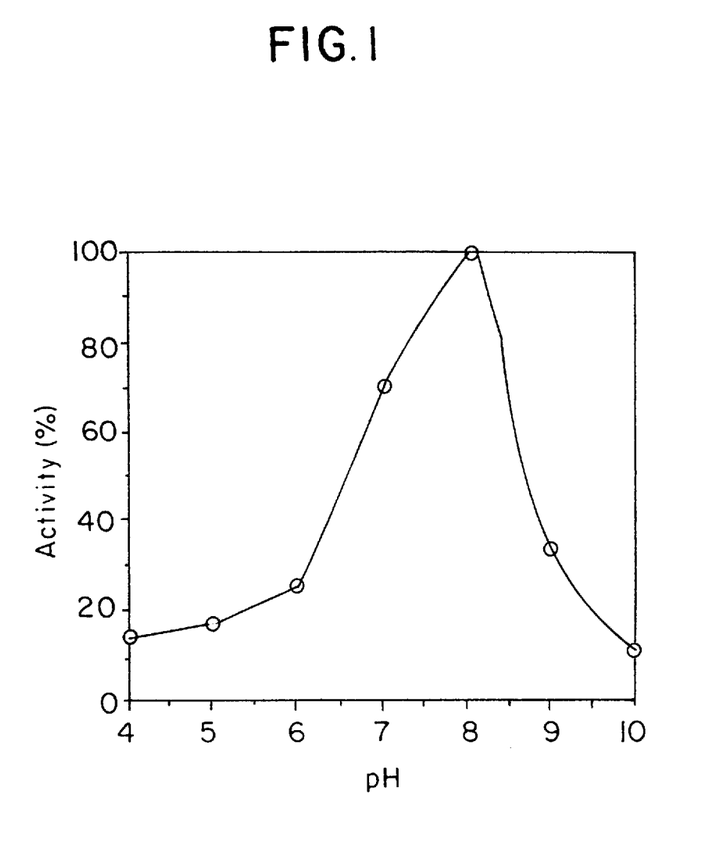
FIG. 1 is a graph showing optimum pH of agarase 0107.

Gel of 0.2% low-melting-point agarose (produced by Sigma) in a volume of 90 μl was adjusted to pH 4 and 5 (acetate buffer), 6 and 7 (phosphate buffer), 8 (Tris-hydrochloric acid buffer), and 9 and 10 (glycine-sodium hydroxide buffer). To the gel, 10 μl of a solution containing β-agarase A (0.2 μg/μl) was added. The mixed solution was incubated at 30° C. for 5 minutes. After the incubation, 100 μl of copper reagent was added therein, and the solution was heated in boiling water for 10 minutes. After the heating, the solution was cooled rapidly with water, 100 μl of Nelson reagent was added therein, and then distilled water was added to make the total volume 2.5 ml. After 60 minutes, the absorbance at 660 nm was determined. As a result, the optimum pH was found to be from 7 to 8.5, from neutral to alkalescent, as shown in FIG. 1.

(4) Optimum temperature

Figure 2:
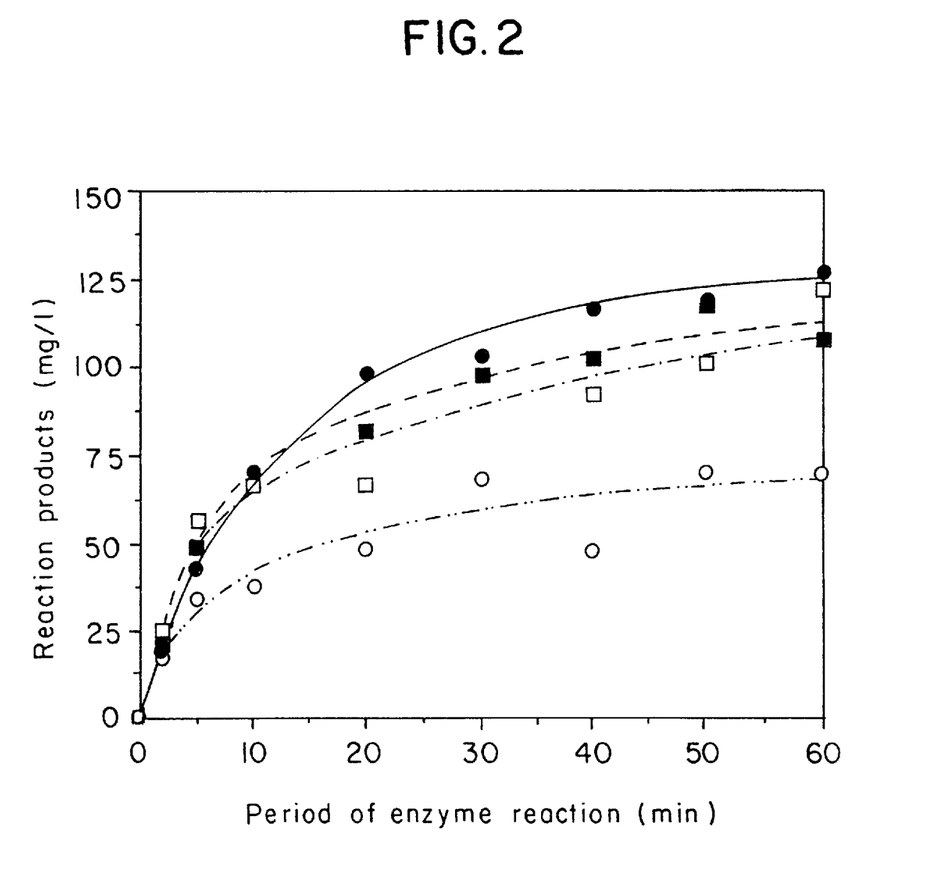
FIG. 2 is a graph showing optimum temperature of agarase 0107.

Gel of 0.2% low-melting-point agarose (produced by Sigma) in a volume of 90 μl was dissolved in 20 mM Tris-hydrochloric acid buffer (pH 8.0). To this solution, 10 μl of a solution which contained β-agarase A (0.08 μg/μl) was added. The mixed solution was incubated at 25° C. for 2, 5, 10, 20, 30, 40, 50 and 60 minutes. The reaction products were measured as the yield of reducing sugar by the Somogyi-Nelson method. Similarly, the amount of reducing sugar of the reactants at 30°, 35°, and 40° C. was determined. As a result, the amount of the reactant at 30° C. was found to be greatest; hence, the optimum temperature to obtain oligosaccharides was determined to be 30° C. This is shown in FIG. 2.

(5) pH stability

The activity of an enzymatic solutions which were adjusted to pH 3.6 to 5.6 (acetate buffer), 5.5 to 7.6 (phosphate buffer), 7.5 to 9 (Tris-hydrochloric acid buffer), and 9 to 10 (glycine-sodium hydroxide buffer) was determined according to the enzymatic activity determination method; the activity in each pH was defined to be 100% and used as the initial value. Furthermore, each enzyme solution was stored at 4° C. for a week, and the residual activity was determined; the pH range maintaining not less than 80% of the initial value was checked. The range was found to be of from 6 to 9.

(6) Thermal stability

Figure 3:
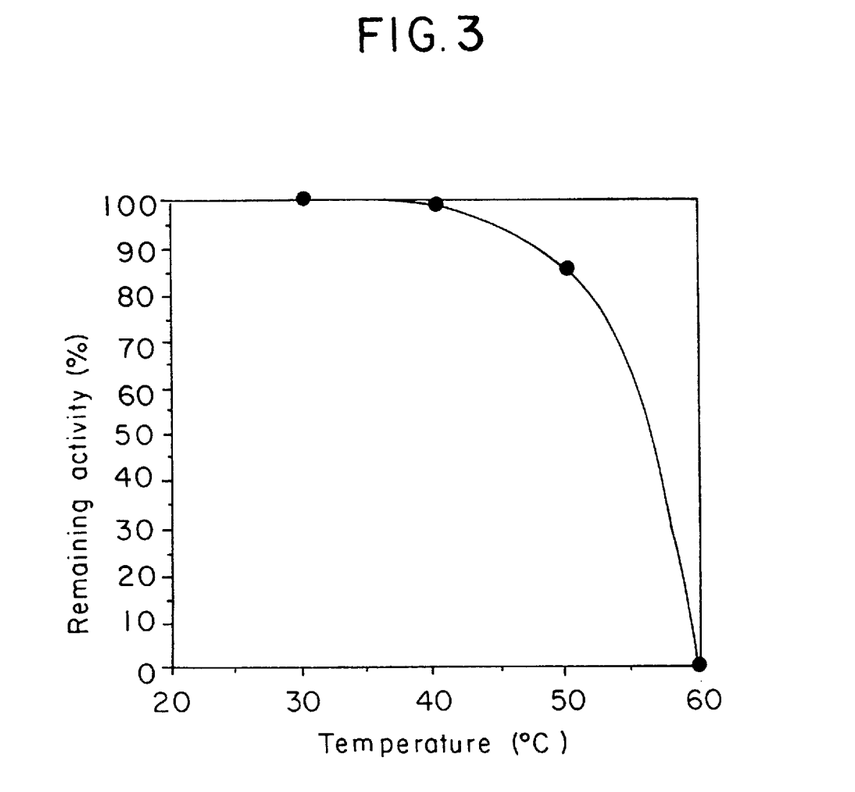
FIG. 3 is a graph showing thermal stability of agarase 0107.

After heating 10 μl of the mentioned enzyme solution (0.1 μg/μl) in water bath at 30°, 40°, 50° and 60° C. for 15 minutes, the enzymatic activity was determined according to the enzymatic activity determination method. When comparing the activities on the basis in which the activity of the enzyme solution determined without heating was supposed to be 100%, the residual activities were found to be approximately 100% at 30° and 40° C., and approximately 85% at 50° C., as shown in FIG. 3, At 60° C., the activity was lost nearly completely.

(7) Isoelectric point

Using "Phast Gel IEF4-6.5" produced by Pharmacia, isoelectric point was determined to be approximately 6.3 with "Fast System", an isoelectric point measurement apparatus, manufactured also by Pharmacia.

(8) Molecular weight

The enzyme was subjected electrophoresis, for determining the molecular weight, together with molecular weight markers (phosphorylase of molecular weight 94,000, bovine serum albumin of molecular weight 67,000 and egg albumin of molecular weight 43,000) using a gradient gel of polyacrylamide gel containing SDS that was of a 10 to 20% concentration; thereby, the molecular weight was found to be about 95,000. According to the calculation on the basis of the amino acid sequence estimated from the whole base sequences of a gene of the enzyme, the molecular weight was found to be approximately 105,300. The entire base sequences of the gene of the enzyme are shown in the specification of Japanese Patent Application 5-96549. Thereby, the present enzyme is distinguished from conventionally known agarase.

(9) Amino terminus amino acid sequence

The amino-terminus amino acid sequence of the enzyme was determined according to Edman degradation method. The enzyme solution (0.4 μg/μl) in an volume of 100 μl was dialyzed, using distilled water which contains 0.1% of SDS as an external liquid for the dialysis, the enzyme solution was analyzed, using the amino acid sequence analyzer, 477A Protein Sequencer (Manufactured by Applied Biosystems) to determine 7 amino acids sequence at the amino terminus of the enzyme. The result showed that the sequence was: Ala→Thr→Leu→Val→Thr→Ser→Phe (SEQ ID NO:1)

(10) Other characteristics

Solubility: soluble in water.

Ultraviolet absorption: λmax=280 nm.

*Vibrio sp.* JT0107-L4, which is the bacterium producing the above-mentioned agarase 0107, is isolated from seawater and has the following microbiological characteristics.

Microbiological characteristics:

1) Form

For the cells grown in Marine Broth 2216 medium:

(A) The form of cells is a curved-rod, the size of which is 0.25–1.2 μm×0.5–2.5 μm.

(B) The cells have mobility and flagella.

(C) The gram stain is negative.

(D) Spores are not formed.

2) Growth

When cultured with Marine Broth 2216 plate medium:

(A) The cells grow well at a range of from 18° to 25° C.

(B) The cells develop pigmentation which is pale yellow in color.
(C) The agar gel is liquefied in accordance with the growth of the cell.
When cultured with Marine Broth 2216 liquid medium:
(D) The cells grow vigorously at the pH of 7, 8 and 9.
3) Physiological properties.

| (A) O-F test | F |
|---|---|
| (B) Catalase test | positive |
| (C) Oxidase test | positive |
| (D) Gas formation from glucose | none |
| (E) Voges-Proskauer reaction | negative |
| (F) Methylred reaction | positive |
| (G) Gelatin hydrolysis | occurring |
| (H) Esculin hydrolysis | occurring |
| (I) Nitrate reduction performance | having |
| (J) Facultative anaerobic | |

*Vibrio sp.* JT0107-L4 was deposited to National Institute of Bioscience and Human-Technology, Agency of Industrial Science and Technology, MITI, as FERM BP-4541, on Mar. 6, 1991.

For producing the above-mentioned agarase 0107 using *Vibrio sp.* JT0107-L4, liquid culture of the microorganisms is made using agar or agarose as the carbon source. While the culture temperature may be varied within a range where the above-mentioned enzyme can be produced, rotary shaking culture is conducted at 18° to 25° C. usually, preferably shake culture is conducted at 150 rpm at 20° C.; the culture period is from 3 to 8 days, preferably from 5 to 7 days. After the culture completes, the solid matters is removed from the culture solution by centrifugal separation, and the culture supernatant is collected. To the supernatant, ammonium sulfate is added until 80 to 90% saturation, and the secreted proteins are subjected to salting out. The salting-out product is collected by centrifugal separation, and subjected to dialysis using 20 mM Tris-hydrochloric acid buffer (pH 8.0) as the external liquid. The dialyzed sample is applied to strong anion exchange columns, called "QAE-Toyopearl" and "Mono-Q"; thereby, the proteins are eluted in sequence by linear concentration gradient method using sodium chloride, and agarase 0107 alone is separated.

While "α-agarase which acts specifically on oligosaccharides derived from agarose" used in the present invention is not limited in particular provided that the enzyme hydrolyzes the α-1,3 bond between D-galactose and 3,6-anhydro-L-galactose and acts specifically on oligosaccharides derived from agarose, α-agarase derived from microorganisms belonging to the genus of Vibrio which hydrolyze the α-1,3 bond between D-galactose and 3,6-anhydro-L-galactose of oligosaccharides derived from agarose having not more than 6 monosaccharide units is preferred; specific examples thereof include α-NAOS hydrolase derived from the above-mentioned *Vibrio sp.* JT0107-L4.

α-NAOS hydrolase is novel α-agarase. The present inventions provide also the novel α-agarase.

Physical and chemical characteristics of α-NAOS hydrolase derived from *Vibrio sp.* JT0107-L4, which is an example of the α-agarase used in the processes of the present inventions, are shown hereunder.
(1) The enzymatic activity determination method
The activity determination of purified or partially purified products of this enzyme is conducted as follows. After an enzyme reaction with neoagarobiose as the substrate, the amount of degraded neoagarobiose is calculated from the amount of intact neoagarobiose which is determined by HPLC. Details are as follows.

A 0.1% solution of neoagarobiose dissolved in 20 mM potassium phosphate buffer (pH 7.8) is prepared. This solution, as the substrate, in a volume of 90 μl was mixed with 10 μl of the enzyme solution. The mixed solution is incubated at 30° C. for 5 to 30 minutes, preferably for 10 minutes; the reaction is stopped by heating in boiling water for 1 minute. This reaction solution in a volume of 10 μl is applied to a column, Capcell pak C-18 (manufactured by Shiseido) which is of 4.5 mm in internal diameter and 250 mm in length, and eluted at a flow rate of 1 ml/min using water as the eluent; the amount of neoagarobiose not degraded by the enzyme reaction, which has a retention time of about 4.5 minutes, is quantified. The amount of degraded neoagarobiose is calculated inversely from the value in this measurement, assuming that the amount of enzyme degrading 1 μmol neoagarobiose per minute is 1 U.
(2) Substrate specificity and function
In 20 mM potassium phosphate buffer (pH 7.8), each substrate of neoagarobiose, neoagarotetraose, neoagarohexaose and agarose is adjusted to a concentration of 0.3%, and an enzyme reaction was done at 30° C. Table 1 shows each activity percentage, supposing the degradation activity of neoagarobiose as 100.

TABLE 1

| Substrate | Degradation Activity (%) |
|---|---|
| Neoagarobiose | 100 |
| Neoagarotetraose | 14 |
| Neoagarohexaose | 37 |
| Agarose | 0 |

Figure 4:
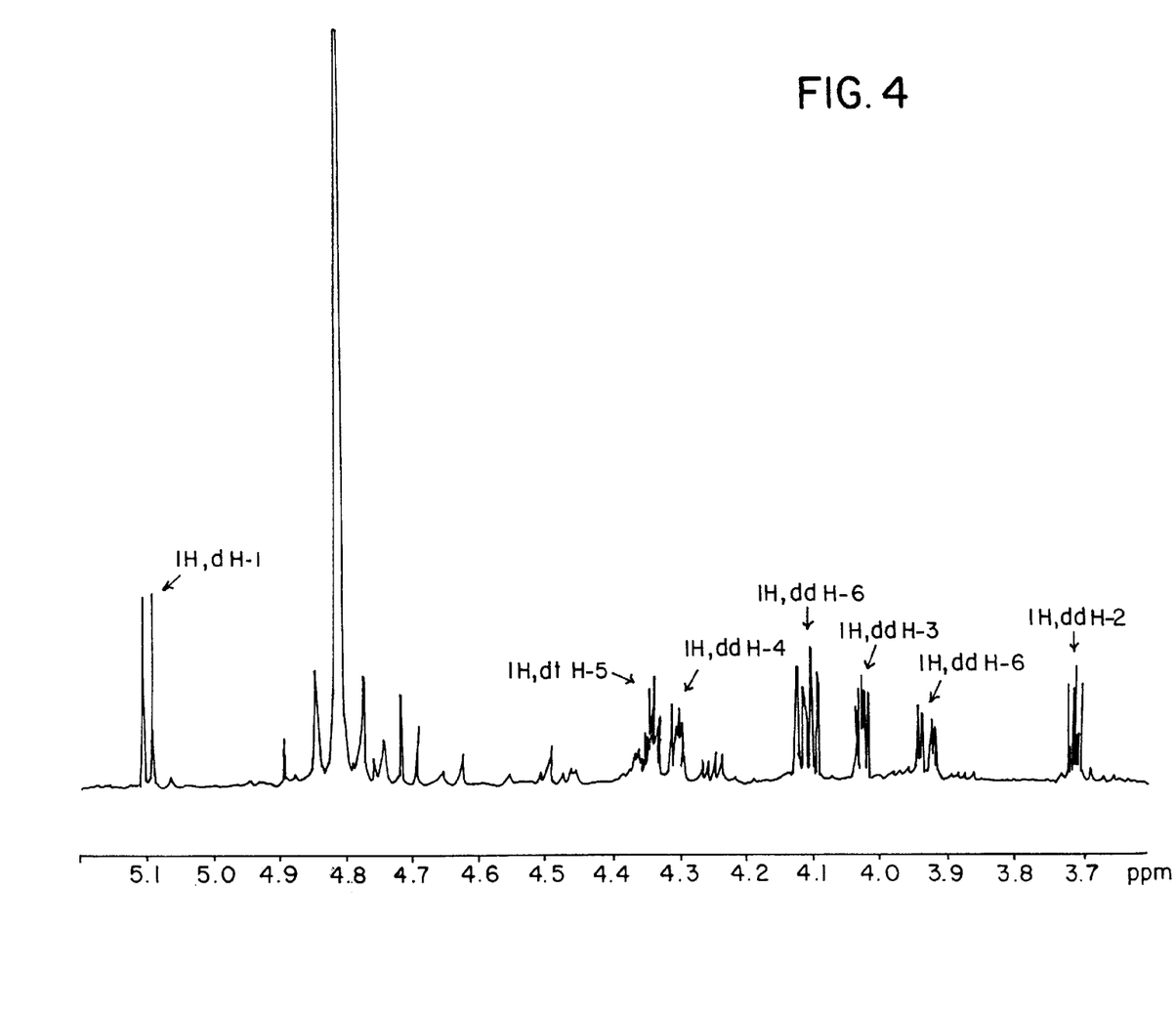
FIG. 4 is a $^1$H-NMR spectrum of 3,6-anhydro-L-galactose.

Specification of the mode of action of α-NAOS hydrolase
The enzyme solution (50 μg/ml) in a volume of 10 μl was added to the 90 μl of 0.3% neoagarohexaose solution, and the mixture was incubated in a constant temperature water bath at 30° C. for 3 hours. The reaction product taken in a volume of 10 μl was applied to a column called "Capcell pak C-18" (manufactured by Shiseido) of 4.5 mm inner diameter and 250 mm length, and eluted out with water eluent at a flow rate of 1 ml/min. The main reaction products had about from 6.5 to 7.2 minutes of retention time. This fraction was taken separately and analyzed by thin-layer chromatography by use of a developing solvent consisting of butanol:ethanol:water=3:1:1; the reaction product that had a spot at Rf=0.21 was verified. This fraction was subjected to freeze-drying, then the mass was determined to be 792 by a fast atom bombardment mass spectrometer. Thus, the reaction product contained in this fraction was concluded to be a pentasaccharide that is agaropentaose, cleavage product of non-reducing end 3,6-anhydro-L-galactose. On the other hand, the pentasaccharide of molecular weight 774 that may be formed by the cleavage of reducing end D-galactose was not found. Most preferential reaction product of the enzyme reaction of 0.2% neoagarotetraose solution had a mass number of 486. From these facts, the reaction product corresponding to this mass number was found to be the trisaccharide agarotriose that is the cleavage product of non-reducing end 3,6-anhydro-L-galactose. On the other hand, the trisaccharide of molecular weight 468 that may be formed by the cleavage of reducing end D-galactose was not found. Furthermore, it was found that the reaction products of the enzyme reaction of the 0.2% neoagarobiose solution were D-galactose and 3,6-anhydro-L-galactose from the $^1$H-NMR determination. From these experiment, the α-NAOS hydrolase was concluded to be a new exo form enzyme, which can recognize the non-reducing end 3,6- anhydro-L-galactose and can hydrolyze α-1,3 bond. ¹H-NMR spectrum of 3,6-anhydro-L-galactose is shown in FIG. 4.

(3) Optimum pH

Figure 5:
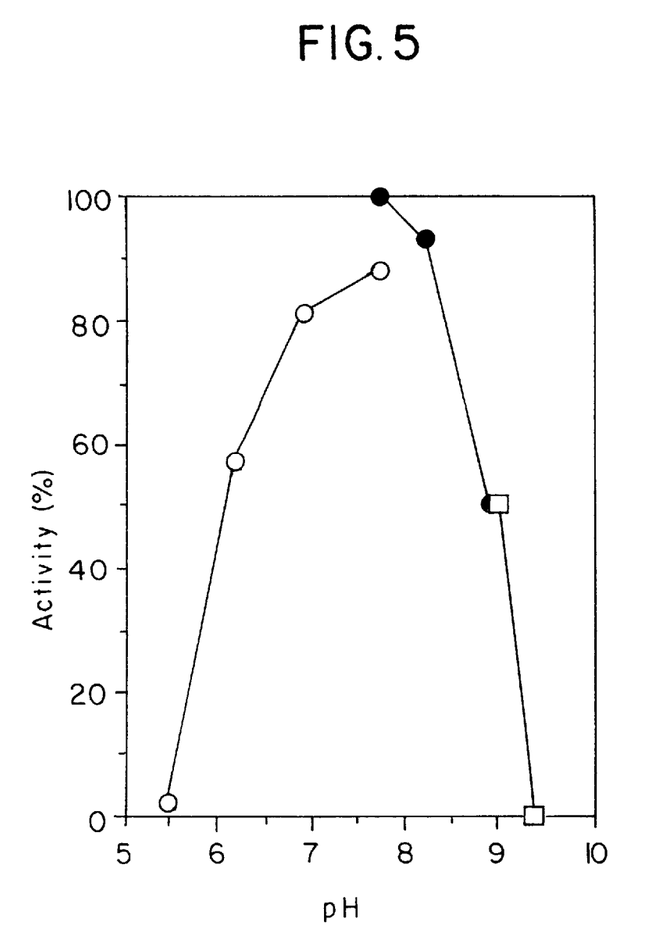
FIG. 5 is a graph showing optimum pH of α-NAOS hydrolase.

The enzyme solution (40 μg/ml) in a volume of 10 μl was added to 90 μl of 0.1% neoagarobiose solution, that was preliminarily adjusted from pH 5.5 to pH 7.7 (phosphate buffer), from pH 7.7 to pH 8.9 (Bicine-sodium hydroxide buffer), from pH 9.0 to pH 9.4 (glycine-sodium hydroxide buffer). The mixture was incubated at 30° C. for 10 minutes, then heated in a boiling water for 1.0 minutes for stopping the reaction. The reaction solution taken in a volume of 10 μl was applied to Capcell pak C-18 (manufactured by Shiseido) of 4.5 mm inner diameter and 250 mm length, and eluted by water eluent in 1 ml/min flow rate, and determined the unreacted neoagarobiose that had about 4.5 minutes of retention time. Relative activity value at each pH, assuming that maximum activity at the pH where degrading capacity for neoagarobiose is 100%, is shown in FIG. 5. As a result, the optimum pH was found to be from 7 to 8.4, from neutral to alkalescent, as shown in FIG. 5.

(4) Optimum temperature

The temperature, at which the enzyme showed least loss of activity and showed the enzyme reaction rate was fastest, was 30° C.

(5) Stability pH stability

Solutions of this enzyme were prepared with the buffers used for determination of the optimum pH, and kept at 30° C. for 30 minutes. Thereafter, activity was determined for each solution. The activity when heat was not applied was supposed to be 100%. Assuming the range of pH stability is the range where residual activity exceeds 80%, the pH stability was recognized to be from pH 6 to 9.

Thermal stability.

Figure 6:
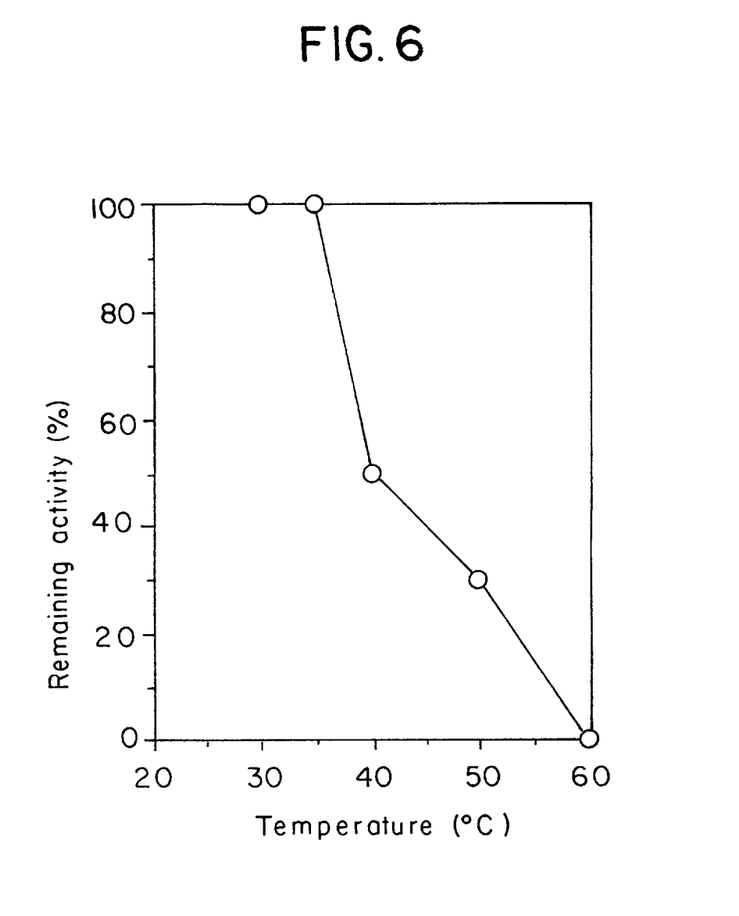
FIG. 6 is a graph showing thermal stability of α-NAOS hydrolase.

The enzyme solution (40 μg/ml) in a volume of 10 μl was heated for 5 minutes in a water bath at 30° C., 35° C., 40° C., 50° C., 60° C., and added to 90 μl of 0.1% neoagarobiose solution (pH 7.8), then kept at 30° C. for 10 minutes for the enzyme reaction. Thereafter, the solution was heated for 1 minute in boiling water for stopping the reaction. The reaction solution taken in a volume of 10 μl was analyzed for the activity. The enzyme activity when heat was not done was supposed to be 100%. The remaining activity after the heating was compared by this standard. The result is: about 100% for 30° C., 35° C.;, and about 50% for 40° C. The activity was nearly completely lost at 60° C. This result is shown in FIG. 6.

(6) The Michaelis constant and the maximum velocity

Neoagarobiose consisting of 3,6-anhydro-L-galactose and D-galactose through α-1,3 bond was used as the substrate. Various substrate solutions of different concentration were prepared. Therein, 10 μl of the enzyme solution (40 μg/ml) was added. The enzyme activity was determined according to the enzymatic activity determination method. The reciprocal of the substrate concentration and the reciprocal of the corresponding enzymatic activity were plotted in two dimensional coordinate; thereby, Lineweaver-Burk equation was determined. From the equation, the Michaelis constant was found to be 4.28±5.0 mM, and the maximum velocity was found to be 87 U/mg-protein.

(7) Molecular weight

The molecular weight was determined by SDS-polyacrylamide gel electrophoresis method and by gel filtration method. In the SDS-polyacrylamide gel electrophoresis method, according to normal procedures, gel having a 10% concentration of polyacrylamide gel including SDS, and molecular weight markers (myosin for molecular weight 200,000, β-galactosidase for molecular weight 116,000, bovine serum albumin for molecular weight 66,000, aldolase for molecular weight 42,000, carbonic anhydrase for molecular weight 30,000) were used. The molecular weight was determined from the mobility, and found to be about 42,000. In the gel filtration method, a gel filtration column called "Superdex 200" manufactured by Pharmacia and molecular weight markers (immunoglobulin G for molecular weight 160,000, human serum albumin for molecular weight 67,000, β-lactoglobulin for molecular weight 35,000, cytochrome C for molecular weight 12,400) were used for the gel filtration; thereby, the amount of the eluted proteins was determined. Then the gel filtration of the enzyme was made. The amount of the eluted enzyme was compared with that of the eluted proteins. From the comparison, the molecular weight was determined, and found to be about 84,000 (±16,000).

(8) Amino terminus amino acid sequence

The amino terminus amino acid sequence of the enzyme was determined by the Edman degradation. The enzyme solution (1 μ/μl) in a volume of 10 μl was processed by 10% SDS-polyacrylamide gel electrophoresis, and the enzyme was adsorbed on the membrane Biodyne A (manufactured by Nippon Pole) by the western blot technique; then 10 amino acids sequence at the amino terminus of the enzyme was determined by 477A Amino Acid Sequencer and 120A Protein Sequencer (manufactured by Applied Biosystems). The result showed that the sequence was: Ser→Gly→Thr→Gly→Ser→Lys→Leu→Ser→Leu→Ala (SEQ ID NO:2)

(9) Other characteristics

Solubility : soluble in water

Ultraviolet absorption spectrum: λmax=280 nm.

The α-agarase that is used in the present inventions belongs to the genus of Vibrio, and can be obtained by gathering α-agarase which is grown and accumulated in the culture by culturing microorganisms capable to produce α-agarase in a culture medium.

Any microorganisms may be used provided that the microorganism belongs to the genus of Vibrio and can produce α-agarase. One of the example is *Vibrio sp.* JT0107-L4 mentioned before.

The culture medium is what contains nitrogen source, minerals and carbon sources such as agarose and agar that are usable for the microorganisms mentioned above.

Commercially available agar and agarose can be used. Carbon source other than agar and agarose includes meat extract, degradation product of casein, tryptone, and peptone; preferably, peptone is used.

As for nitrogen source, yeast extract is used.

As for salts, sodium chloride, ferric citrate, magnesium chloride, sodium sulfate, calcium chloride, potassium chloride, sodium carbonate, sodium bicarbonate, potassium bromide, strontium chloride, sodium borate, sodium silicate, sodium fluoride, ammonium nitrate, disodium hydrogenphosphate and their combination can be used.

The medium called "Marine Broth 2216" (manufactured by Difco) containing all the components mentioned above except agar and agarose is usable when agar and agarose are added. Artificial seawater such as Sealife (manufactured by MarineTech) containing the minerals mentioned above properly, can be used as the medium when peptone, yeast extract, agar and the like are added. Concentration from 0.1 to 1.5% of agar or agarose is preferable; depending on the concentration of agar or agarose, the state of the medium (solid or liquid) is selected. Liquid medium of concentration from 0.1 to 0.4% is preferable for the enzyme production, and solid medium of concentration from 1.2 to 1.5% is preferable for the preservation of this strain.

Depending on the medium composition, some different culture condition is applied; preferable temperature is from 15° to 30° C. and more preferable temperature is from 20° to 25° C.; preferable pH is from 7.0 to 8.5, and more preferable pH is from 7.8 to 8.2; and preferable culture period is from 15 to 48 hours, and more preferably from 18 to 24 hours.

Target enzyme is an intracellular enzyme, and can be separated and purified from disrupted cell that is disrupted by conventional methods; for example ultra sonication, French press method, glass beads method, Dyno-Mill KDL apparatus may be used. Among them, Dyno-Mill KDL apparatus is preferable. For example, solid material may be separated from disrupted cell by centrifugal separation or filtration; thereafter, to the supernatant, salt solution such as saturated from 30 to 90%, preferably from 40 to 70%, of ammonium sulfate solution is added for salting out the target enzyme. The salted out product is suspended in a proper buffer (pH 7.0–8.5), preferably in potassium phosphate buffer (pH 7.8), dialyzed repeatedly several times using the same buffer, in a volume of from 50 to 200 times as much as the suspension, as the external liquid, then desalted and redissolved. The product may be purified up to forming electrophoretically single band grade, by combining column chromatography with anion exchange column, gel filtration column, hydroxyapatite column and the like.

Now, a preferable embodiment of the First Process of the present invention is explained.

What contains from 0.1 to 1.0 wt %, more preferably from 0.1 to 0.5 wt %, of agarose produced from agar is used as the substrate; therein, from 1 to 300 U, more preferably from 5 to 50 U, of β-agarase A is added per 1 g of the substrate. The reaction is made at a temperature from 30° to 45° C., more preferably from 30° to 40° C., with pH 7 to pH 8.5, more preferably pH 7.7 to pH 8.3. Normally, the reaction period is from 3 to 24 hours, although it varies significantly depending on the volume of substrate, pH, temperature, agitation speed, and polymerization degree of the target oligosaccharide, and the like.

Then, from 0.3 to 300 U, more preferably from 3 to 150 U, of α-agarase is added per 1 g of the substrate. The reaction is made at a temperature from 25° to 35° C., more preferably from 25° to 30° C., with pH 7.5 to pH 8.5, more preferably pH 7.8 to pH 8.2. Normally, the reaction period is from 1 to 20 hours, although it varies significantly depending on the volume of substrate, pH, temperature, agitation speed and the like.

Resulting reaction product contains from 70 to 100 wt % of monosaccharides and oligosaccharides having not more than 5 monosaccharide units. The content ratio of monosaccharides in the reaction product can be enhanced by way of increasing the amount of β-agarase A per 1 g of the substrate and prolonging the reaction period, whereby the amount of product neoagarobiose is increased; the content ratio of pentasaccharides and/or trisaccharides can be enhanced by decreasing the amount of β-agarase A and shortening the reaction period, whereby the selectivity to pentasaccharides and/or trisaccharides is raised.

Agaropentaose, which is a pentasaccharide, consisting of D-galactose (β-1,4) 3,6-anhydro-L-galactose (α-1,3) D-galactose (β-1,4) 3,6-anhydro-L-galactose (α-1,3) D-galactose, and having molecular weight of 792; agarotriose which is a trisaccharide, consisting of D-galactose (β-1,4) 3,6-anhydro-L-galactose (α-1,3) D-galactose, and having molecular weight of 486; and 3,6-anhydro-L-galactose, which is a monosaccharide; can be obtained from the reaction product by separation and purification.

Examples of techniques for the separation and purification include column chromatography using silica gel and column chromatography using active carbon.

When the β-agarase A and the α-agarase are derived from the same microorganism, in the case of the First Process of the present invention, it is not necessary to change the reaction condition such as pH and temperature for both enzymes; the reactions may be under same conditions. In addition, β-agarase A and the α-agarase may be simultaneously reacted to the agarose. Simplification of the reaction process can be attained by this way. Specific example is the case in which the α-agarase (α-NAOS hydrolase) and β-agarase A (agarase 0107) produced by *Vibrio sp.* JT0107-L4 mentioned before, are used.

By controlling the reaction conditions of β-agarase A, it is possible to produce selectively even-number oligosaccharides having more than 6 monosaccharide units; by use of such an oligosaccharide as the substrate, the reaction of α-agarase makes it possible to get the odd-number oligosaccharide having the smaller degree of polymerization by one than the even-number oligosaccharide produced selectively.

Now, the Second Process of the present invention is explained.

The Second Process of the present invention is a process for producing oligosaccharides and/or monosaccharides, wherein, β-agarase A and an α-agarase which acts specifically on oligosaccharides derived from agarose are allowed to react with a substrate which contains an oligosaccharide derived from agarose.

Here, "substrate which contains an oligosaccharide derived from agarose" includes the case where the substrate contains an oligosaccharide only and the case where the substrate contains an oligosaccharide and other additives. As mentioned above, the oligosaccharide is a saccharide from disaccharide to octasaccharide, but a saccharide from disaccharide to hexasaccharide is more preferable.

Neoagarohexaose, neoagarotetraose, neoagarobiose are included in this "oligosaccharide derived from agarose". Such an oligosaccharide may be a commercially available product (manufactured by Sigma).

Examples of synthetic process for producing such oligosaccharide include a reaction of agarose with the β-agarase A mentioned before; and a conventional process in which agarose is reacted with the β-agarase (hereinafter referred to as "agarase B") that reacts with polysaccharides derived from agarose but does not react with the oligosaccharide having 6 or less monosaccharide units.

Specific examples of the agarase B include an agarase produced by *Pseudomonas sp* N-7 (FERM P-9884), and an agarase produced by *Pseudomonas atlantica* (manufactured by Sigma) Physical and chemical properties of the agarase B, microbiological characteristics of the microorganism and the production method of the enzyme are reported in details in literature (JP-A 1-228465, L. M. Morrice et al, European Journal of Biochemistry, 135, 553–558 (1983) etc.).

Concerning α-agarase and β-agarase A, what has been described for the First Process of the present invention is applicable.

Now, a preferable embodiment of the Second Process of the present invention will be explained.

What contains from 0.1 to 2.0 wt %, more preferably from 0.3 to 1.0 wt %, of oligosaccharide derived from agarose is used as the substrate. Therein, from 0.5 to 20 U, more preferably from 1 to 10 U, of β-agarase A per 1 g of the substrate is added. The reaction is made at a temperature from 30° to 45° C., more preferably from 30° to 40° C., with pH 7 to pH 8.5, more preferably pH 7.7 to pH 8.3. Normally, the reaction period is from 3 to 24 hours, although it varies significantly depending on the volume of substrate, pH, temperature, agitation speed and the like.

Then, from 0.5 to 50 U, preferably from 1.5 to 15 U, of α-agarase is added per 1 g of the substrate. The reaction is made at a temperature from 25° to 35° C., preferably from 25° to 30° C., with pH 7.5 to pH 8.5, preferably pH 7.8 to pH 8.2. Normally, the reaction period is from 1 to 20 hours, although it varies significantly depending on the volume of substrate, pH, temperature, agitation speed and the like.

In the Second Process of the present invention, it is possible to allow β-agarase A and α-agarase to react with an oligosaccharide derived from agarose, as is the case of the First Process of the present invention. If the both enzymes are derived from the same microorganism, simplification of the reaction process is possible in the same way as in the First Process of the present invention. A specific example is the case where the α-agarase (α-NAOS hydrolase) and β-agarase A (agarase 0107) prepared from *Vibrio sp.* JT0107-L4 mentioned before are used.

Resulting reaction product contains from 70 to 100 wt % of monosaccharides and oligosaccharides having not more than 5 monosaccharide units. The content ratio of monosaccharides in the reaction product can be enhanced by using neoagarotetraose as the substrate and controlling the reaction conditions of β-agarase A (agarase 0107) within the scope mentioned above, whereby the neoagarotetraose is completely degraded to neoagarobiose. The content ratio of pentasaccharides in the reaction product can be increased by using neoagarotetraose as the substrate, and controlling the reaction condition of the β-agarase A (agarase 0107) within the scope mentioned above, whereby neoagarotetraose is partially degraded to neoagarohexaose. The content ratio of trisaccharide in the reaction product can be increased by using neoagarohexaose as the substrate, and controlling the reaction condition of the β-agarase A (agarase 0107) within the scope mentioned above, whereby neoagarohexaose is partially degraded to neoagarotetraose.

Agaropentaose, agarotriose, and D-galactose and 3,6-anhydro-L-galactose, both of which are monosaccharides; can be obtained by separation and purification of the mixture mentioned above.

Now, the Third Process of the present invention is explained.

The Third Process of the present invention is a process for producing oligosaccharides and/or monosaccharides, wherein, α-agarase which acts specifically on oligosaccharides derived from agarose is allowed to react with a substrate which contains an oligosaccharide derived from agarose. Here, "a substrate which contains an oligosaccharide derived from agarose" is the same as that explained in the Second Process of the present invention, and "α-agarase" is the same as that explained in the First Process of the present invention.

According to the Third Process of the present invention, monosaccharides and/or oligosaccharides having low polymerization grade and having the non-reducing terminal of D-galactose can be produced.

At the first step, an oligosaccharide, derived from agar or agarose, such as agarooctaose, agarohexaose, agarotetraose, neoagarotetraose, neoagarohexaose, neoagarotetraose, preferably from a disaccharide to hexasaccharide, are used as the row material separately or in desired combination. By allowing the α-agarase mentioned above, for example α-NAOS hydrolase, to react with raw material, oligosaccharides of lower polymerization degree and/or monosaccharide can be produced. The raw material used here is not necessarily of pure grade but also may be what is commercially available. What is prepared by acid-degradation of agar or what is prepared from commercially available agarase may be also used. The raw material is dissolved in a solvent like phosphate buffer; the concentration is adjusted from 0.1 to 1.0%, preferably from 0.2 to 0.6%. The α-agarase is added to the mixture, which is allowed to react at 25° to 35° C. Oligosaccharides having various polymerization degree can be produced by controlling the reaction time optionally, usually from 2 to 24 hours, and by adding suitable amount of enzyme. The product oligosaccharides and/or monosaccharides in the reaction mixture can be separated and purified for respective polymerization grades by column chromatography using active carbon or silica gel. The α-agarase in this reaction need not be purified also, and enough effect can be expected by partially purified α-agarase.

The oligosaccharides obtained in these processes include agarobiose, agarotriose, agaropentaose; the monosaccharide products are 3,6-anhydro-L-galactose and D-galactose.

The β-agarase A and α-agarase used in the present invention need not be fully purified; enough effect can result by partially purified ones.

According to the present invention, oligosaccharides, derived from agar or agarose, having not more than 5 of the polymerization degree, and 3,6-anhydro-L-galactose and D-galactose both of which are monosaccharides have become effectively produced.

BRIEF DESCRIPTION OF THE DRAWINGS

○ Enzyme reaction at 25° C.

● Enzyme reaction at 30° C.

□ Enzyme reaction at 35° C.

■ Enzyme reaction at 40° C.

○ Phosphate buffer

● Bicine-sodium hydroxide buffer

□ Glycine-sodium hydroxide buffer

DESCRIPTION OF THE PREFERRED EMBODIMENTS

Now, the present invention is explained in details by way of examples, however, the present invention is not limited to thereby.

EXAMPLE 1

Preparation of α-NAOS hydrolase

Artificial sea water (trade name "Sealife": manufactured by was MarineTech) was prepared in a volume of 500 ml. To this solution, 5 g of peptone (manufactured by Nippon Seiyaku) and 1 g of yeast extract (manufactured by Difco)

were added. The pH of the solution was adjusted to 8.0, which was then placed in a 3,000 ml Erlenmeyer flask. Therein, 1 g of agar (manufactured by Kyokuto) was added. The content was subjected to sterilization in an autoclave. *Vibrio sp.* JT0107-L4 stored at −80° C. in 40% glycerol, was melted at room temperature; 1 ml of the melted sample was inoculated to the sterilized solution, which was then cultured at 25° C. for 24 hours at 150 rpm. The resulting solution was used as a preliminary culture solution.

The culture was carried out in the following procedures. Artificial sea water (trade name "Sealife": manufactured by was MarineTech) was prepared in a volume of 3,000 ml using a 5,000 ml jar fermenter vessel, to which 60 g of peptone (manufactured by Nippon Seiyaku) and 12 g of yeast extract (manufactured by Difco) was added, the pH of which was adjusted to 8.0. Therein, 12 g of agar (manufactured by Kyokuto) was added. The content was subjected to sterilization in an autoclave. The preliminary culture solution mentioned above was inoculated in a volume of 30 ml to the sterilized solution, which was then cultured at 25° C. for 20 hours at 600 rpm. The cell thus obtained was collected by a Sharpless centrifugal separator. The wet weight collected was about 50 g. The cell was suspended in a 20 mM phosphate buffer (pH 7.8), and the total volume was made to 100 ml. The suspension was mixed with 150 ml of glass beads of 0.2 mm diameter, and disrupting of the cell was made by Dyno-Mill KDL apparatus at 3,000 rpm for 15 minutes.

The suspension of disrupted cell was subjected to 20,000×g centrifugal separation for 60 minutes to remove glass beads and cell debris. Into 100 ml of resultant supernatant, ammonium sulfate was added so as to be 40% saturation. Resulting precipitate was removed with 6,000×g for 30 minutes. Ammonium sulfate was further added to the supernatant so as to be 70% saturation. Precipitate formed was collected by 6,000×g centrifugal separation for 30 minutes and was suspended in 30 ml of 20 mM phosphate buffer (pH 7.8). The suspension was subjected to dialysis three times in total with 5,000 ml of this buffer for desalting and redissolution.

This dialysis liquid was applied to a column (2.2 cm×9 cm) filled with 34 ml of a strong anion exchange resin, called QAE-Toyopearl (manufactured by Tosoh), preliminarily equilibrated with 20 mM phosphate buffer, and was eluted by linear concentration gradient method (total eluate volume: 300 ml) from a 20 mM phosphate buffer (pH 7.8) to a 20 mM phosphate buffer (pH 7.8) containing 0.5 M sodium chloride. Thereby, a 50 ml fraction was collected eluting between 0.3M and 0.4M of the sodium chloride concentration.

This fraction was diluted into 200 ml with the same buffer and divided into two pieces of 100 ml fraction. Each fraction was applied to a column (1.0 cm×10 cm) having a carrier of strong anion exchange resin, called Mono-Q (manufactured by Pharmacia), preliminarily equilibrated with 20 mM phosphate buffer, and was eluted by linear concentration gradient method mentioned above (total eluate volume: 120 ml); thereby, a 16 ml fraction was collected eluting between 0.3M and 0.4M of the sodium chloride concentration. Again, this fraction was diluted into four times as much as the volume with the same buffer. Chromatography using Mono-Q was repeated, and an 8 ml fraction which eluted between 0.3M and 0.35M. This fraction was divided into 4 pieces of 2 ml each. Each of them was concentrated into 0.5 ml by using Centricon 50, a centrifugal ultrafiltration membrane manufactured by Grace Japan, was applied to a column (1.0 cm×30 cm) using gel filtration carrier, called Superdex 200 (manufactured by Pharmacia), and was eluted with 20 mM phosphate buffer (pH 7.8) containing 0.1M sodium chloride; thereby, fractions eluting from 13.6 ml to 14.4 ml were obtained.

This product was made into a volume of 4 ml with reagent water, called Milli Q, which was made from distilled water with Milli Q System (manufactured by Millipore). A column filled with hydroxyapatite, called HCA-8010G (manufactured by Mitsui Toatsu Chemicals), was used for elution by linear concentration gradient method (total eluate volume: 15 ml) from 10 mM phosphate buffer (pH 6.8) to 175 mM phosphate buffer (pH 6.8). The fraction eluting from 7.5 ml and 8.5 ml were obtained.

This fraction was subjected electrophoresis with polyacrylamide gel containing sodium dodecyl sulfate (SDS); thereby the target enzyme was proved to have a molecular weight of about 42,000. Specific activity of this fraction increased by 350 times compared with that of the disrupted cell. Total activity was 4.4 U, and the activity yield was 2.5%.

EXAMPLE 2

Preparation of agarase 0107

A culture solution in a volume of 1,000 ml of *Vibrio sp.* JT0107-L4 was subjected to centrifugal separation, and about 900 ml of culture supernatant and solid matter were separated. For the purpose of salting out protein, ammonium sulfate was gradually added, while stirring, to the culture supernatant until 90% saturation. The mixture was left at 5° C. overnight. Resulting salting-out product was collected by centrifugal separation and subjected to dialysis against 3,000 ml of 20 mM Tris-hydrochloric acid buffer (pH 8.0) through a cellophane tube as the dialysis membrane. The dialysis was carried out at 5° C. for 18 hours during which the external liquid was exchanged twice. The sample obtained was applied to a column (1 cm×2.5 cm) filled with QAE Toyopearl (a strong anion exchange resin manufactured by Tosoh) which was preliminarily equilibrated with 20 mM Tris-hydrochloric acid buffer (pH 8.0). This sample was eluted by linear concentration gradient method (total eluate volume: 4 ml) from 20 mM Tris-hydrochloric acid buffer (pH 8.0) to 20 mM Tris-hydrochloric acid buffer containing 0.5M sodium chloride (pH 8.0), and the fraction of 6 ml which eluted after the sodium chloride concentration became 0.5M. Resulting fraction was made into a volume of 24 ml with addition of 20 mM Tris-hydrochloric acid buffer (pH 8.0), was applied to a column (0.5 cm×5 cm) filled with Mono-Q (a strong anion exchange resin manufactured by Pharmacia) which was preliminarily equilibrated by the above-mentioned buffer, and was eluted by the linear concentration gradient method (total eluate volume: 15 ml) mentioned above.

Agarase 0107 was eluted and separated at 0.5M sodium chloride concentration. The yield of agarase 0107, determined by absorbance of ultraviolet absorption at 280 nm wavelength, was 0.91 mg per 1,000 ml of culture solution. Enzymatic activity was determined and found to be a titer of about 6.3 U per 1 mg of enzyme. Here, 1 U is defined as the enzymatic activity able to get an amount of reducing sugar which corresponds to 1 micro mol of galactose per minute. This result reveals that the activity per unit weight of agarase 0107 increased by about 48 times than that of the culture supernatant.

The agarase 0107 obtained was subjected electrophoresis, for determining the molecular weight, together with molecular weight markers (phosphorylase of molecular weight 94,000, bovine serum albumin of molecular weight 67,000 and egg albumin of molecular weight 43,000) using a gradient gel of polyacrylamide gel containing SDS that was of a 10 to 20% concentration; thereby, the molecular weight of agarase 0107 was found to be about 95,000. The isoelectric point of agarase 0107 was determined by "Phast Gel System" manufactured by Pharmacia, and found to be about 6.3.

EXAMPLE 3

Preparation of 3,6-anhydro-L-galactose

An amount of 100 mg of agarose was dissolved in 20 ml of water. Into this solution, a solution of 0.2 ml of Trishydrochloric acid buffer (pH 8.0) which dissolved 2 U of agarase 0107 isolated and purified from *Vibrio sp.* JT0107-L4 was added. The resultant solution was incubated at 30° C. for 18 hours in a constant-temperature water bath, then a solution of 1 ml of potassium phosphate buffer (pH 7.8) which dissolved 3.8 U of α-NAOS hydrolase isolated and purified from *Vibrio sp.* JT0107-L4 was added therein. The resultant solution was incubated at the same temperature for 4 hours. The reaction solution was subjected to freeze-drying, then added by 5 ml of methanol. The soluble content was applied to a column (15 mmφ×840 mm) using a carrier of silica gel called Iatrobeads (manufactured by Yatoron), and elution by linear concentration gradient method (total eluate volume: 960 ml) from a solution of the composition of chloroform:methanol:water=70:28:2 to a solution of the composition of chloroform:methanol:water=53:45:2 was made. When the composition was between chloroform:methanol:water=68.5:29.5:2 and 66.7:31.3:2, a reaction product was confirmed by thin layer chromatography at Rf=0.7–0.8 (developing solvent; butanol:ethanol:water=3:1:1). The solvents of this eluate was removed by distillation, and 20 mg of the substance was obtained. An amount of 50 μg of this substance was supplied to a fast atom bombardment mass spectrometer for determining the mass; thereby, the mass number of this substance was found to be 162. From these facts in combination of the analytical results shown later in Example 6, the substance was identified as 3,6-anhydro-L-galactose. However, 3,6-anhydro-L-galactose may exists, having a molecular weight of 180, in the form of a diol in which two hydroxyl groups are attached to the 1-position carbon, in place of a pyranose form closed ring structure. The structure of 3,6-anhydro-L-galactose is shown below.

EXAMPLE 4

Preparation of agarotriose

An amount of 30 mg of neoagarohexaose was dissolved in 10 ml of phosphate buffer of pH 7.8. Into this solution, a solution of 0.1 ml of potassium phosphate buffer (pH 7.8) which dissolved 0.1 U of agarase 0107 isolated and purified from *Vibrio sp.* JT0107-L4 was added. The resultant solution was incubated at 30° C. for 3 hours, then a solution of 0.1 ml of phosphate buffer (pH 7.8) which dissolved 1.5 U of α-NAOS hydrolase isolated and purified from *Vibrio sp.* JT0107-L4 was added therein. The resultant solution was incubated at 30° C. for 5 hours. The reaction solution was applied to an activated carbon column (5 mmφ×50 mm), which was then washed with 1 ml of water and 1 ml of 10% ethanol followed by elution with 3 ml of 24% ethanol. The solvents of the 24% ethanol fraction were removed by distillation using a rotary evaporator. Thereafter, freeze-drying was applied and the weight was determined; the weight was 11.4 mg. This reaction product was analyzed by thin layer chromatography; thereby, a substance of Rf=0.3 (developing solvent; butanol:ethanol:water=3:1:1) was confirmed. In addition, the mass number of the reaction product was determined using a fast atom bombardment mass spectrometer and found to be 486. From these facts, the substance was identified as agarotriose. The yield of the resulting agarotriose was calculated as 76%. The structure of agarotriose is shown below.

EXAMPLE 5

Preparation of agaropentaose

An amount of 30 mg of neoagarohexaose was dissolved in 10 ml of phosphate buffer of pH 7.8. Into this solution, a solution of 0.1 ml of phosphate buffer (pH 7.8) which dissolved 1.5 U of α-NAOS hydrolase isolated and purified from *Vibrio sp.* JT0107-L4 was added. The resultant solution was incubated at 30° C. for 5 hours; thereby, neoagarohexaose was decomposed. The reaction solution was applied to an activated carbon column (5 mmφ×50 mm), which was then washed with 1 ml of water and 1 ml of 10% ethanol followed by elution with 3 ml of 30% ethanol. The solvents of the 30% ethanol fraction were removed by distillation using a rotary evaporator. Thereafter, freeze-drying was applied and the weight was determined; the weight was 13.5 mg. This reaction product was analyzed by thin layer chromatography; thereby, a substance of Rf=0.21 (developing solvent; butanol:ethanol:water=3:1:1) was confirmed. In addition, the mass number of the reaction product was determined using a fast atom bombardment mass spectrometer and found to be 792. From these facts, the substance was identified as agaropentaose. The yield of the resulting agaropentaose was calculated as 80%. The structure of agaropentaose is shown below.

EXAMPLE 6

Preparation of 3,6-anhydro-L-galactose and determination of the structure

An amount of 100 mg of neoagarobiose was dissolved in 9.5 ml of water. Into this solution, a solution of 0.5 ml of phosphate buffer (pH 7.8) which dissolved 1.9 U of α-NAOS hydrolase isolated and purified from *Vibrio sp.* JT0107-L4 was added. The solution was incubated at 30° C. for 3 hours. The reaction solution was subjected to freeze-drying. Then, the sample was suspended in 2.5 ml of a solvent of which composition was chloroform:methanol:water=35:14:11. The resultant was applied to a column (20 mmφ×240 mm) using a carrier of silica gel called Iatrobeads (manufactured by Yatoron), and elution by linear concentration gradient method (total eluate volume: 960 ml) from a solution of the composition of chloroform:methanol:water=70:28:2 to a solution of the composition of chloroform:methanol:water=53:45:2 was made. When the composition was between chloroform:methanol:water=68.1:29.9:2 and 65.5:32.5:2, 3,6-anhydro-L-galactose was confirmed by thin layer chromatography at Rf=0.7–0.8 (developing solvent; butanol:ethanol:water=3:1:1). The solvents of this eluate was removed by distillation, and 49 mg of the substance was obtained. The eluted substance and the acetyl derivative of this substance were analyzed by an $^1$H-nuclear magnetic resonance spectrometer; thereby, the substance was identified as 3,6-anhydro-L-galactose. The yield was 98%. The acetylation of this substance was made by allowing 49 mg of this substance in 1 ml of pyridine solvent to react with 1 ml of acetic anhydride at room temperature for 18 hours. The resultant acetylated substance was applied to a column (20 mmφ×240 mm) using silica gel carrier, and was eluted by linear concentration gradient method (total eluate volume: 320 ml) from a solution of the composition of hexane:ethyl acetate=80:20 to a solution of the composition of hexane::ethyl acetate=10:90. When the solvent composition was hexane:ethyl acetate=30:70, a reaction product of Rf=0.5 (developing solvent; benzene:ethyl acetate=7:3) was confirmed by thin layer chromatography. This reaction product was analyzed by an $^1$H-nuclear magnetic resonance spectrometer.

---

What is claimed is:

1. A purified α-agarase which hydrolyzes the α-1,3 bond between the non-reducing terminal 3,6-anhydro-L-galactose and the adjacent D-galactose of neoagaro-oligosaccharides of six or fewer monosaccharide units and has the following physical and chemical characteristics:
 (a) Optimum pH: 7–8.4; and
 (b) Optimum temperature: 30° C.

2. A purified α-agarase which has the following physical and chemical characteristics:
 (1) Function and Substrate specificity:
   hydrolyzes the α-1,3 bond between the non-reducing terminal 3,6-anhydro-L-galactose and the adjacent D-galactose of neoagaro-oligosaccharides of six or fewer monosaccharide units;
 (2) Optimum pH: 7–8.4;
 (3) Optimum temperature: 30° C.;
 (4) pH stability: 6–9;
 (5) Thermal stability:
   to maintain about 100% of the initial activity after being heated at 35° C. for 5 minutes and to maintain about 50% of the initial activity after being heated at 40° C. for 5 minutes;
 (6) Molecular weight: about 42,000 (determined by 10% SDS-polyacrylamide gel electrophoresis); and
 (7) Amino terminus amino acid sequence:
   Ser→Gly→Thr→Gly→Ser→Lys→Leu→Ser→Leu→Ala (Seq. ID No. 2).

3. A process for producing the α-agarase of claim 1, which comprises the steps of culturing in a medium *Vibrio sp.* JT0107-L4 (FERM BP-4541) and recovering the α-agarase which is produced and accumulated in the culture.

4. A process for producing oligosaccharides and/or monosaccharides, comprising contacting a β-agarase which acts on both polysaccharides and oligosaccharides derived from agarose and an α-agarase of claim 1 which acts specifically on oligosaccharides derived from agarose with a substrate which contains agarose.

5. The process according to claim 4, wherein said β-agarase which acts on both polysaccharides and oligosaccharides derived from agarose is the β-agarase which has the following physical and chemical characteristics:
 (1) Function:
   to endo catalyze a reaction of degrading at least agar and agarose;
 (2) Substrate specificity:
   to hydrolyze agar and agarose but not to act on carrageenan and alginic acid;
 (3) Optimum pH: 7–8.5 (30° C.);
 (4) Optimum temperature: 30° C.;
 (5) pH stability: 6–9;
 (6) Thermal stability:
   to maintain about 85% of the maximum activity when heated at 50° C. for 15 minutes;
 (7) Isoelectric point: about 6.3;
 (8) Molecular weight: about 95,000 (determined by 10–20% SDS-polyacrylamide gel electrophoresis); and
 (9) Amino terminus amino acid sequence:
   Ala→Thr→Leu→Val→Thr→Ser→Phe (SEQ ID NO:1).

6. The process according to claim 4 wherein the oligosaccharide produced is agaropentaose.

7. The process according to claim 4 wherein the oligosaccharide produced is agarotriose.

8. The process according to claim 4 wherein the monosaccharide produced is 3,6-anhydro-L-galactose.

9. The process according to claim 4 wherein said α-agarase is an α-agarase which has the following physical and chemical characteristics:
 (1) Function and Substrate specificity:
   hydrolyzes the α-1,3 bond between the non-adjacent reducing terminal 3,6-anhydro-L-galactose and the adjacent D-galactose of neoagaro-oligosaccharides of six or fewer monosaccharide units;
 (2) Optimum pH: 7–8.4;
 (3) Optimum temperature: 30° C.;
 (4) pH stability: 6–9;
 (5) Thermal stability:
   to maintain about 100% of the initial activity after being heated at 35° C. for 5 minutes and to maintain about 50% of the initial activity after being heated at 40° C. for 5 minutes;
 (6) Molecular weight: about 42,000 (determined by 10% SDS-polyacrylamide gel electrophoresis); and
 (7) Amino terminus amino acid sequence:
   Ser→Gly→Thr→Gly→Ser→Lys→Leu→Ser→Leu→Ala.

10. A process for producing oligosaccharides and/or monosaccharides, comprising contacting a β-agarase which acts on both polysaccharides and oligosaccharides derived from agarose and an α-agarase of claim 1 which acts specifically on oligosaccharides derived from agarose with a substrate which contains an oligosaccharide derived from agarose.

11. The process according to claim 10, wherein said β-agarase has the following physical and chemical characteristics:
 (1) Function:
   to endo catalyze a reaction of degrading at least agar and agarose;
 (2) Substrate specificity:
   to hydrolyze agar and agarose but not to act on carrageenan and alginic acid;
 (3) Optimum pH: 7–8.5 (30° C.);
 (4) Optimum temperature: 30° C.;
 (5) pH stability: 6–9;
 (6) Thermal stability:
   to maintain about 85% of the maximum activity when heated at 50° C. for 15 minutes;

(7) Isoelectric point: about 6.3;

(8) Molecular weight: about 95,000 (determined by 10–20% SDS-polyacrylamide gel electrophoresis); and (9) Amino terminus amino acid sequence:
Ala→Thr→Leu→Val→Thr→Ser→Phe (Seq ID NO:1).

12. The process according to claim 10, wherein said substrate which contains an oligosaccharide derived from agarose is a substrate which contains neoagarohexaose.

13. The process according to claim 10 wherein the oligosaccharide produced is agaropentaose.

14. The process according to claim 10 wherein the oligosaccharide produced is agarotriose.

15. The process according to claim 10 wherein the monosaccharide produced is 3,6-anhydro-L-galactose.

16. A process for producing oligosaccharides and/or monosaccharides, comprising contacting a β-agarase which acts on both polysaccharides and oligosaccharides derived from agarose and the α-agarase of claim 2 with a substrate which contains an oligosaccharide derived from agarose.

17. A process for producing oligosaccharides and/or monosaccharides, comprising contacting α-agarase of claim 1 which acts specifically on oligosaccharides derived from agarose with a substrate which contains an oligosaccharide derived from agarose.

18. The process according to claim 17, wherein said substrate which contains an oligosaccharide derived from agarose is a substrate which contains neoagarohexaose.

19. The process according to claim 17 wherein the oligosaccharide produced is agaropentaose.

20. The process according to claim 17 wherein the oligosaccharide produced is agarotriose.

21. The process according to claim 17 wherein the monosaccharide produced is 3,6-anhydro-L-galactose.

22. A purified α-agarase from *Vibrio sp.* JT0107-L4.

* * * * *